(12) United States Patent
Blair et al.

(10) Patent No.: US 8,714,149 B2
(45) Date of Patent: May 6, 2014

(54) AIRFLOW ADAPTOR FOR A BREATH-ACTUATED DRY POWDER INHALER

(75) Inventors: Julian Alexander Blair, Stradbally (IE); Daniel Buck, Waterford (IE); Jan Geert Hazenberg, Kilkenny (IE); Xian-Ming Zeng, London (GB)

(73) Assignee: Norton Healthcare Limited, West Yorkshire (GB)

( * ) Notice: Subject to any disclaimer, the term of this patent is extended or adjusted under 35 U.S.C. 154(b) by 474 days.

(21) Appl. No.: 12/941,204

(22) Filed: Nov. 8, 2010

(65) Prior Publication Data

US 2011/0108030 A1 May 12, 2011

Related U.S. Application Data

(60) Provisional application No. 61/298,705, filed on Jan. 27, 2010.

(30) Foreign Application Priority Data

Nov. 6, 2009 (GB) .................................. 0919465.5

(51) Int. Cl.
  *A61M 15/00* (2006.01)
  *A61M 16/00* (2006.01)
  *B05D 7/14* (2006.01)
  *B65D 83/06* (2006.01)
(52) U.S. Cl.
  USPC ..................................................... 128/203.15
(58) Field of Classification Search
  USPC ............. 128/203.15, 203.19, 203.21, 203.23, 128/203.24
  See application file for complete search history.

(56) References Cited

U.S. PATENT DOCUMENTS

| | | | | |
|---|---|---|---|---|
| 5,301,666 A | * | 4/1994 | Lerk et al. | 128/203.15 |
| 5,647,349 A | * | 7/1997 | Ohki et al. | 128/203.15 |
| 6,341,605 B1 | * | 1/2002 | Ohki et al. | 128/203.15 |
| 6,681,768 B2 | * | 1/2004 | Haaije de Boer et al. | 128/203.15 |
| 6,748,947 B2 | | 6/2004 | Keane et al. | |
| 7,708,014 B2 | * | 5/2010 | Yamashita et al. | 128/203.15 |
| 2003/0015195 A1 | * | 1/2003 | Haaije de Boer et al. | 128/203.15 |
| 2006/0169280 A1 | * | 8/2006 | Yama et al. | 128/203.21 |
| 2006/0231096 A1 | * | 10/2006 | Ohki et al. | 128/203.21 |
| 2010/0108058 A1 | * | 5/2010 | Glusker et al. | 128/200.14 |

FOREIGN PATENT DOCUMENTS

| | | | |
|---|---|---|---|
| WO | WO 01/04118 A2 | 1/2001 | |
| WO | WO 01/97889 A2 | 12/2001 | |
| WO | WO 2008051621 A2 | * 5/2008 | ............ A61M 15/00 |

* cited by examiner

*Primary Examiner* — Jackie Ho
*Assistant Examiner* — Mark K Han
(74) *Attorney, Agent, or Firm* — RatnerPrestia

(57) ABSTRACT

An airflow adaptor for a breath-actuated dry powder inhaler. The airflow adaptor includes a conduit having a proximal end and a distal end, wherein the proximal end allows fluid communication from a deagglomerator outlet port to the distal end of the conduit, and wherein the airflow adaptor further includes provisions for allowing air to flow from a proximal end of the adaptor to a distal end of the adaptor independently of the airflow in the conduit when a breath induced low pressure is applied to the distal end of the airflow adaptor.

11 Claims, 6 Drawing Sheets

AIRFLOW ADAPTOR FOR A BREATH-ACTUATED DRY POWDER INHALER

CROSS-REFERENCE TO RELATED APPLICATIONS

This application claims priority to Great Britain Patent Application No. GB0919465.5, filed on Nov. 6, 2009, and U.S. patent application Ser. No. 61/298,705, filed on Jan. 27, 2010, the contents of such patent applications bring incorporated by reference herein in their entirety.

FIELD OF THE INVENTION

The present invention relates to an airflow adaptor for a breath-actuated dry powder inhaler. In particular, the present invention relates to an airflow adaptor for a deagglomerator of a breath-actuated dry powder inhaler; a deagglomerator for a breath-actuated dry powder inhaler; a method for deagglomerating dry powder medicaments; and a method for modifying airflow through the outlet port of a deagglomerator of a breath-actuated dry powder inhaler.

BACKGROUND TO THE INVENTION

Breath-actuated dry powder inhalers are used to deliver medicament to the respiratory tracts of patients. Typically such inhalers comprise a reservoir, or reservoirs, for storing dry powder medicament, means for aerosolising the dry powder medicament for inhalation, and means for delivering the aerosolised medicament to the patient, such as a mouthpiece. Typically, in use, the dry powder medicament is dispensed from a reservoir and then aerosolised as a result of a breath-induced low pressure at the mouthpiece. Once aerosolised, the medicament will generally leave the inhaler through the mouthpiece and be inhaled.

Known dry powder medicament is composed of very small particles and often provided in a composition including a carrier, such as lactose. Consequently, non-defined agglomerates or aggregates of the dry powder medicament may form at random prior to being delivered to the patient. There has therefore been a need for breath-actuated dry powder inhalers with means for breaking down the agglomerates of medicament, or medicament and carrier, prior to inhalation.

Deagglomerators for breath-actuated dry powder inhalers are disclosed in WO01/97889.

There is, however, a continued need to reduce the flow rate dependence of breath-actuated dry powder inhalers and, in particular, the flow rate dependence of the delivered dose of the medicament they deliver. In particular, there is a need to ensure that different patient groups receive substantially the same delivered dose from the same breath-actuated dry powder inhaler.

There is also a need for providing breath-actuated dry powder inhalers, and in particular those with deagglomerators, which provide better delivered dose characteristics. Particularly, there is a need for breath-actuated dry powder inhalers which provide improved delivered dose uniformity.

These and other problems are addressed by an airflow adaptor for a breath-actuated dry powder inhaler; a deagglomerator for a breath-actuated dry powder inhaler; a method for de-agglomerating dry powder in a breath-actuated dry powder inhaler; and a method for modifying airflow through the outlet port of a deagglomerator according to the independent claims. Further advantageous embodiments are disclosed in the dependent claims.

SUMMARY OF THE INVENTION

Accordingly, in a first aspect the present invention provides an airflow adaptor for a breath-actuated dry powder inhaler. The airflow adaptor comprises a conduit having a proximal end and a distal end, wherein the proximal end of the conduit allows fluid communication from a deagglomerator outlet port to the distal end of the conduit. The airflow adaptor further comprises means for allowing air to flow from a proximal end of the adaptor to a distal end of the adaptor independently of the airflow in the conduit when a breath induced low pressure is applied to the distal end of the airflow adaptor.

It has surprisingly been found that by providing an airflow adaptor with means for allowing air to flow from a proximal end of the adaptor to a distal end of the adaptor independently of the airflow in the conduit when a breath induced low pressure is applied to the distal end of the airflow adaptor the flow rate dependency of the device is reduced.

Without being bound by any particular theory, this is believed to be because while the airflow adaptor of the invention causes an increase in the volumetric flow rate, i.e. the volume of air passing through the airflow adaptor per second, for a given breath induced low pressure at the distal end of the airflow adaptor, it actually lowers the linear flow rate through the conduit, i.e. the velocity of air passing through the conduit, for a given breath-induced low pressure. The consequence of this is that a given increase or decrease, i.e. a change, in the breath-induced low pressure at the distal end of the airflow adaptor results in a reduced change in the linear flow rate through the conduit. Thus, the flow rate dependence of the breath-actuated dry powder inhaler is reduced.

It has further been surprisingly found that by providing the means for allowing air to flow from a proximal end of the adaptor to a distal end of the adaptor independently of the airflow in the conduit when a breath induced low pressure is applied to the distal end of the airflow adaptor, the dose delivery characteristics of a breath-actuated dry powder inhaler, and in particular the breath-actuated dry powder inhaler's delivered dose uniformity, are improved.

This is particularly surprising because, as explained above, for a given breath induced low pressure, the linear flow rate through the conduit is reduced. This would have been expected to reduce the performance of the breath-actuated dry powder inhaler, rather than improve it, because higher flow rates were thought to typically lead to more deagglomeration and better dose delivery.

Without being bound by any particular theory, the improvement is believed to be because, in use, the spread of medicament leaving the conduit is limited by the secondary airflow formed by the means for allowing air to flow from a proximal end of the adaptor to a distal end of the adaptor independently of the airflow in the conduit when a breath induced low pressure is applied to the distal end of the airflow adaptor.

In a preferred embodiment of the invention, the means for allowing air to flow from a proximal end of the adaptor to a distal end of the adaptor independently of the airflow in the conduit when a breath induced low pressure is applied to the distal end of the airflow adaptor comprises at least one second conduit. Preferably, the at least one second conduit comprises two, three, four or six conduits. Typically, the conduit and at least one second conduit are substantially parallel, preferably parallel.

Multiple second conduits are preferred because, in use, they provide improved control of the medicament leaving the conduit and therefore better delivered dose characteristics. Without being bound by any particular theory, two second conduits will control medicament spread in one plane, three second conduits will control the medicament spread in two planes, and four second conduits will control medicament spread in two planes better than three second conduits. Further conduits provide even more control over medicament spread.

Preferably the distal end of the conduit comprises a first circumferential flange. In an embodiment, the at least one second conduit is in the form of at least one aperture in the first circumferential flange. Preferably, the first circumferential flange comprises two, four or six apertures.

The conduit and/or at least one second conduit may have any cross-sectional shape. Preferably the cross-sectional shape of the conduit and/or at least one second conduit is circular, triangular or square, most preferably circular. The diameter of the conduit and/or at least one second conduit may vary along the length of the conduit and/or at least one second conduit, for instance the conduit and/or at least one second conduit may be frustroconical, although the diameter of the conduit and/or at least one second conduit may also be constant along their length. In preferred embodiments the conduit and/or at least one second conduit are cylindrical.

In a preferred embodiment, the ratio of the sum of the cross-sectional areas of the at least one second conduit to the cross-sectional area of the conduit is such that when a breath induced low pressure is applied to the distal end of the airflow adaptor at least about 5%, preferably at least about 15%, preferably at least about 20%, more preferably from about 5% to about 50%, more preferably from about 15% to about 40%, and even more preferably from about 20% to about 30% of the resulting airflow is through the at least one second conduit.

Typically, the sum of the cross-sectional areas of the apertures in the first circumferential flange will be from about 0.75 $mm^2$ to about 20 $mm^2$, more preferably from about 5 $mm^2$ to about 16 $mm^2$, and even more preferably from about 9 $mm^2$ to about 11 $mm^2$. Where the at least second conduit is in a form other than apertures in the first circumferential flange, the sum of cross-sectional areas of the at least one second conduits may also be in the above preferred ranges.

Typically, the conduit will have a cross-sectional area of from about 25 $mm^2$ to about 50 $mm^2$, preferably from about 30 $mm^2$ to about 45 $mm^2$, and most preferably from about 35 $mm^2$ to about 45 $mm^2$.

In a further embodiment, the airflow adaptor comprises a second circumferential flange at the proximal end of the airflow adaptor; typically the second circumferential flange comprising at least one aperture, preferably four apertures. Typically the number of apertures in the second circumferential flange will match the number of apertures in the first circumferential flange.

Preferably, the sum of the cross-sectional areas of the apertures in the second circumferential flange will be from about 0.75 $mm^2$ to about 20 $mm^2$, more preferably from about 5 $mm^2$ to about 16 $mm^2$, and even more preferably from about 9 $mm^2$ to about 11 $mm^2$. Typically the sum of the cross-sectional areas of the apertures in the second circumferential flange will be the same as that of those in the first circumferential flange.

In a further embodiment, the ratio of the sum of the cross-sectional areas of the apertures in the second circumferential flange to the cross-sectional area of the conduit is such that when a breath induced low pressure is applied to the distal end of the airflow adaptor at least about 5%, preferably at least about 15%, more preferably from about 5% to about 50%, more preferably from about 15% to about 40%, and even more preferably from about 20% to about 30% of the resulting airflow is through the apertures.

Typically the airflow adaptor is in the form of a single unitary structure, although in some embodiments it may comprise more than one part. Preferably, the airflow adaptor is in the form of a single, injection moulded unitary structure.

In a further aspect the invention provides a deagglomerator for a breath-actuated dry powder inhaler comprising an airflow adaptor according to the first aspect of the invention. Typically the deagglomerator comprises an inner wall defining a swirl chamber for deagglomerating the dry powder.

In an embodiment the deagglomerator preferably comprises an inner wall defining a swirl chamber extending along an axis from a first end to a second end; a dry powder supply port in the first end of the swirl chamber for providing fluid communication between a dry powder delivery passageway of an inhaler and the first end of the swirl chamber; at least one inlet port in the inner wall of the swirl chamber adjacent to the first end of the swirl chamber providing fluid communication between a region exterior to the de-agglomerator and the first end of the swirl chamber; an outlet port providing fluid communication between the second end of the swirl chamber and the airflow adaptor; whereby a breath induced low pressure at the distal end of the airflow adaptor causes air to flow into the swirl chamber through the dry powder supply port and the inlet port.

In addition to the benefits described above for the airflow adaptor, it has been further found that by introducing the airflow adaptor in combination with a deagglomerator the performance of the deagglomerator itself can be improved. Without being bound by any particular theory, it is believed that this is because the lower linear flow of air through the conduit as a result of the airflow adaptor has the effect reducing changes in the velocity of the airflowing through the swirl chamber of the deagglomerator as a result of corresponding changes in the breath induced low pressure. During use, this has the effect of reducing the flow rate dependence of the delivered fine particle dose.

Furthermore, the lower linear flow rate through the conduit may also have the effect of reducing the formation of secondary vortices and stalled airflow within the swirl chamber, and areas of high sheer on the walls of the swirl chamber, both of which may adversely affect the performance of the deagglomerator.

In an embodiment the deagglomerator further comprises vanes at the first end of the swirl chamber extending at least in part radially outwardly from the axis of the chamber, each of the vanes having an oblique surface facing at least in part in a direction transverse to the axis.

In a further embodiment the at least one inlet port comprises two diametrically opposed inlet ports.

In a still further aspect the invention provides a deagglomerator for a breath-actuated dry powder inhaler, the deagglomerator comprising: an airflow adaptor providing fluid communication between the outlet port and a region exterior to the deagglomerator; an inner wall defining a swirl chamber extending along an axis from a first end to a second end; a dry powder supply port in the first end of the swirl chamber for providing fluid communication between a dry powder delivery passageway of an inhaler and the first end of the swirl chamber; at least one inlet port in the inner wall of the swirl chamber adjacent to the first end of the swirl chamber providing fluid communication between a region exterior to the de-agglomerator and the first end of the swirl chamber; an outlet port providing fluid communication between the second end and the airflow adaptor; and wherein the airflow adaptor comprises at least one swirl chamber by-pass port for allowing air to flow independently of the swirl-chamber from a region exterior to the deagglomerator to a distal end of the airflow adaptor when a breath induced low pressure is applied to the distal end of the airflow adaptor.

Preferably, the breath induced low pressure at the distal end of the airflow adaptor also causes air to flow into the swirl chamber through the dry powder supply port and the inlet port. Typically the at least one swirl chamber bypass port will comprise at least two, preferably four swirl chamber bypass ports.

It has been found that by introducing a swirl chamber by-pass port to a deagglomerator comprising an inner wall defining a swirl chamber, the performance of the deagglomerator can be improved. Without being bound by any particular theory, it is believed that this is because the swirl chamber bypass port lowers the linear flow rate of air through the deagglomerator outlet port. A lower linear flow of air through the outlet port has the effect of reducing fluctuations in the velocity of the airflowing through the swirl chamber of the deagglomerator as a result of changes in the breath induced low pressure. During use, this has the effect of reducing the flow rate dependence of the delivered fine particle dose, i.e. the mass of the active substance below 5 μm. The fine particle dose can be measured according to s. 2.9.18. of the European Pharmacopoeia 6.0 using an Anderson Cascade Impactor.

Additionally, the lower linear flow rate through the outlet port may also have the effect of reducing the formation of secondary vortices and stalled airflow within the swirl chamber, and areas of high sheer on the walls of the swirl chamber, all of which can adversely affect the performance of the deagglomerator.

In an embodiment, the ratio of the sum of the cross-sectional areas of the at least one swirl chamber bypass ports to the cross-sectional area of outlet port is such that that when a pressure breath induced low pressure is applied to the distal end of the airflow adaptor at least about 5%, preferably at least about 15%, more preferably from about 5% to about 50%, more preferably from about 15% to about 40%, and even more preferably from about 20% to about 30% of the resulting airflow is directed through the at least one swirl chamber bypass port.

Typically, the sum of the cross-sectional areas of the at least one swirl chamber bypass ports will be from about 0.75 mm$^2$ to about 20 mm$^2$, more preferably from about 5 mm$^2$ to about 16 mm$^2$, and even more preferably from about 9 mm$^2$ to about 11 mm$^2$.

Typically, the outlet port will have a cross-sectional area of from about 25 mm$^2$ to about 50 mm$^2$, preferably from about 30 mm$^2$ to about 45 mm$^2$, and most preferably from about 35 mm$^2$ to about 45 mm$^2$.

In an embodiment the deagglomerator further comprises vanes at the first end of the swirl chamber extending at least in part radially outwardly from the axis of the chamber, each of the vanes having an oblique surface facing at least in part in a direction transverse to the axis.

In a further embodiment the at least one inlet port comprises two diametrically opposed inlet ports.

In a still further embodiment the airflow adaptor comprises a conduit having a circumferential flange, and wherein the at least one swirl chamber bypass port is in the form of at least one aperture, preferably at least two apertures, more preferably at least four apertures, in the circumferential flange.

In a further aspect the invention provides a breath-actuated dry powder inhaler. Typically a reservoir breath-actuated dry powder inhaler.

In a still further aspect the invention provides a method for de-agglomerating dry powder in a breath-actuated dry powder inhaler, comprising: directing a first breath-actuated airflow for entraining a dry powder from an inhaler into a first end of a swirl chamber extending along a longitudinal axis from the first end to a second end, the first airflow directed in a longitudinal direction; directing a second breath-actuated airflow in a substantially transverse direction into the first end of the swirl chamber such that the first and the second breath-actuated airflows collide and substantially combine; directing a portion of the combined airflows in a spiral path towards the second end of the swirl chamber; delivering all the combined airflows and any dry powder entrained therein through an outlet port in the second end of the swirl chamber to an airflow adaptor; and directing a third breath-actuated airflow to the airflow adaptor, the third breath-actuated airflow having by-passed the swirl chamber.

Preferably, the third breath-actuated airflow is combined with the combined first and second breath-actuated airflows after they have left the airflow adaptor. Typically, the third breath-actuated airflow is combined with the combined first and second breath-actuated airflow in the mouth of a patient.

In an embodiment, the third breath-actuated airflow represents at least about 5%, preferably at least about 15%, more preferably from about 5% to about 50%, more preferably from about 15% to about 40%, and even more preferably from about 20% to about 30% of the airflow leaving the airflow adaptor.

Throughout the description where references are made to percentages they refer to the percent by volume.

In an embodiment, a portion of the combined first and second airflow is deflected off vanes non-rotationally fixedly attached to the first end of the swirl chamber and extending at least in part radially outwardly from the axis of the swirl chamber, wherein each of the vanes has an oblique surface facing at least in part in a direction transverse to the axis, such that the first portion of the combined airflow is deflected in a substantially longitudinal direction towards the second end of the swirl chamber.

In a further aspect the invention provides a method for modifying airflow through the outlet port of a deagglomerator of a dry powder inhaler. The method comprises the steps of providing an airflow adaptor comprising a conduit having a proximal end and a distal end, the airflow adaptor further comprising means for allowing air to flow from a proximal end of the adaptor to a distal end of the adaptor independently of airflow in the conduit; arranging the conduit such that it provides fluid communication from the outlet port of the deagglomerator to the distal end of the conduit; and applying a breath induced low pressure to the distal end of the airflow adaptor such that air flows through the conduit and the means for allowing air to flow from the proximal end of the adaptor to the distal end of the adaptor. Typically, the method for modifying airflow through the outlet port of a deagglomerator will reduce the linear flow rate through the outlet port.

DETAILED DESCRIPTION

Figure 1:
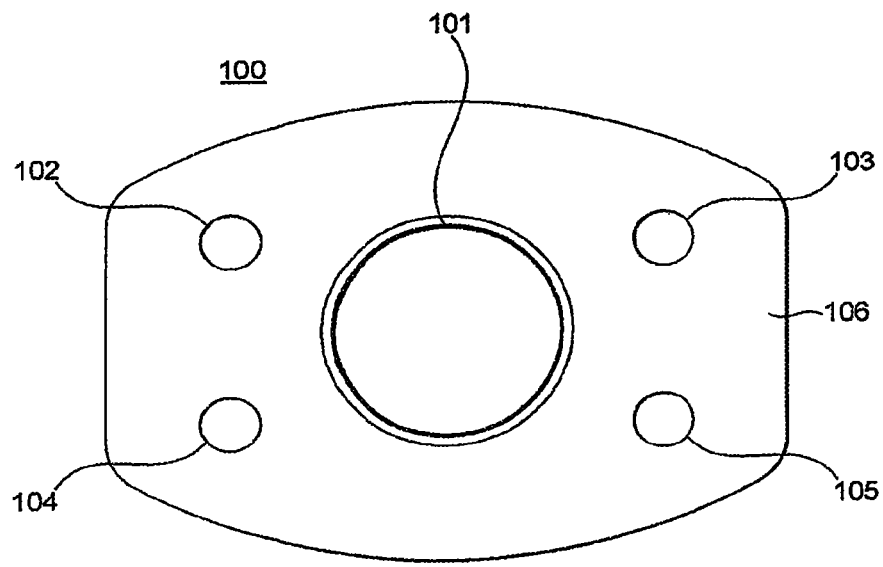
FIG. 1 shows a view of the distal end of an airflow adaptor.
Figure 2:
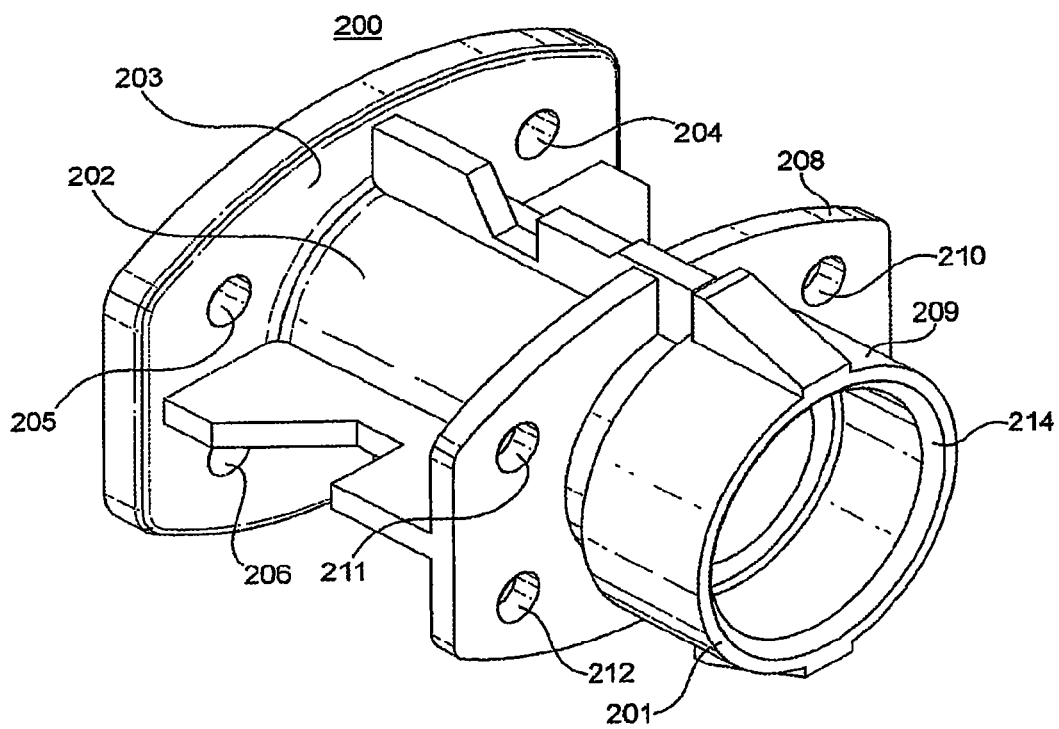
FIG. 2 shows a view of the proximal end of an airflow adaptor.

The present invention provides an airflow adaptor for a breath-actuated dry powder inhaler, the airflow adaptor comprising: a conduit having a proximal end and a distal end, wherein the proximal end allows fluid communication from a deagglomerator outlet port to the distal end of the conduit, and wherein the airflow adaptor further comprises means for allowing air to flow from a proximal end of the adaptor to a distal end of the adaptor independently of the airflow in the conduit when a breath induced low pressure is applied to the distal end of the airflow adaptor.

FIG. 1 shows an airflow adaptor according to the invention, in particular it shows the distal end of the airflow adaptor (100). The airflow adaptor comprises a conduit (101) with a first circumferential flange (106). The conduit shown has a circular cross-section; however, it may have any cross-sectional shape, for instance circular, square or triangular.

The airflow adaptor also comprises means for allowing air to flow from a proximal end of the adaptor to a distal end of the adaptor independently of the airflow in the conduit when a breath induced low pressure is applied to the distal end of the airflow adaptor (102, 103, 104, 105). The means for allowing air to flow from a proximal end of the adaptor to a distal end of the adaptor independently of the airflow in the conduit when a breath induced low pressure is applied to the distal end of the airflow adaptor (102, 103, 104, 105) are in the form of four apertures in the first circumferential flange (106). In alternative embodiments there may be other numbers of apertures, for instance one, two, three, five, six, eight or more. The apertures shown have a circular cross-section; however, they may have any cross-sectional shape, for instance circular, square or triangular.

FIG. 2 shows a view of the proximal end (201) of the airflow adaptor (200). The airflow adaptor comprises a conduit (202) with a first circumferential flange (203). The conduit shown has a circular cross-section; however, it may have any cross-sectional shape, for instance circular, square or triangular.

The airflow adaptor also comprise means for allowing air to flow from a proximal end of the adaptor to a distal end of the adaptor independently of the airflow in the conduit when a breath induced low pressure is applied to the distal end of the airflow adaptor (204, 205, 206, fourth not shown). The means for allowing air to flow from a proximal end of the adaptor to a distal end of the adaptor independently of the airflow in the conduit when a breath induced low pressure is applied to the distal end of the airflow adaptor (204, 205, 206, fourth not shown) are in the form of four apertures in the first circumferential flange (203).

In alternative embodiments there may be other numbers of apertures, for instance one, two, three, five, six, eight or more. The apertures shown have a circular cross-section; however, they may have any cross-sectional shape, for instance circular, square or triangular. The airflow adaptor (200) shown in FIG. 2 further comprises a second circumferential flange (208). The second circumferential flange comprises four apertures (210, 211, 212, fourth not shown). The circumferential flange may, however, comprise any number of apertures, for instance one, two, three, four, six or eight apertures. The apertures shown have a circular cross-section; however, they may have any cross-sectional shape, for instance circular, square or triangular.

The first and second circumferential flanges may be of any shape; however, they are preferably of a shape which enables them mate with the mouthpiece of a dry powder inhaler. Preferably, they mate such that during use air will not flow across the mating surface.

The proximal end (209) of the conduit (202) allows fluid communication from a deagglomerator outlet port to the distal end of the conduit. In particular, the airflow adaptor (200) shown in FIG. 2 has a mating surface (214) for mating with the outlet port of a deagglomerator outlet port. Preferably, they mate such that during use air will not flow across the mating surface. It is understood that in certain embodiments, the outlet port and the airflow adaptor may be a unitary structure.

FIG. 3 shows a view of the proximal end (301) of the airflow adaptor (300). The airflow adaptor comprises a conduit (302) with a first circumferential flange (303). The conduit shown has a circular cross-section; however, it may have any cross-sectional shape, for instance circular, square or triangular.

The airflow adaptor also comprises means for allowing air to flow from a proximal end of the adaptor to a distal end of the adaptor independently of the airflow in the conduit when a breath induced low pressure is applied to the distal end of the airflow adaptor (304, 305, 306, fourth not shown). The means for allowing air to flow from a proximal end of the adaptor to a distal end of the adaptor independently of the airflow in the conduit when a breath induced low pressure is applied to the distal end of the airflow adaptor are in the form of four second conduits (304, 305, 306, fourth not shown) running from the second circumferential flange (308) to the first circumferential flange (309). The second conduits shown have circular cross-sections (310, 311, 312, fourth not shown); however, they may have any cross-sectional shape, for instance circular, square or triangular.

The proximal end (309) of the conduit (302) is suitable for making fluid communication with the outlet port of a deagglomerator of a dry powder inhaler. In particular, the airflow adaptor (300) shown in FIG. 3 has a mating surface (310) for mating with an outlet port of a deagglomerator of a dry powder inhaler. Preferably, they mate such that during use air will not flow across the mating surface. It is understood that in certain embodiments, the outlet port and the airflow adaptor may be a unitary structure.

The airflow adaptor of the invention may be moulded from any suitable polymeric material. Suitable polymeric materials include polypropylene and acrylonitrile butadiene styrene (both available from BASF).

FIG. 4 shows a deagglomerator (400) suitable for including the airflow adaptor (not shown). The deagglomerator (400) comprises: an inner wall (412) defining a swirl chamber (414) extending along an axis (A) from a first end (418) to a second end (420); a dry powder supply port (422) in the first end (418) of the swirl chamber (414) for providing fluid communication between a dry powder delivery passageway of an inhaler and the first end (418) of the swirl chamber (414); at least one inlet port (424, 425) in the inner wall (412) of the swirl chamber (414) adjacent to the first end (418) of the swirl chamber (414) providing fluid communication between a region exterior to the de-agglomerator (400) and the first end (418) of the swirl chamber (414); an outlet port (432) providing fluid communication between the second end (420) of the swirl chamber (414) and an airflow adaptor (not shown); whereby a breath induced low pressure at the distal end of the airflow adaptor (not shown) causes air to flow into the swirl chamber (414) through the dry powder supply port (422) and the inlet port (424,425).

Preferably, the at least one inlet port (424, 425) comprises two diametrically opposed inlet ports (424, 425) that extend in a direction substantially transverse to the axis A and substantially tangential to the circular cross-section of the swirl chamber (414). As a result, airflows, illustrated by arrows 2 and 3 in FIG. 4, entering the swirl chamber (414) through the inlet ports are at least initially directed transverse with respect to the axis A of the swirl chamber and collide with the airflow entering through the supply port (422) to create turbulence. The combined airflows, illustrated by arrow 4 in FIG. 4, then collide with the inner wall (412) of the swirl chamber (414), form a vortex, and create additional turbulence as they move towards the second end (420) of the swirl chamber.

Figure 4:
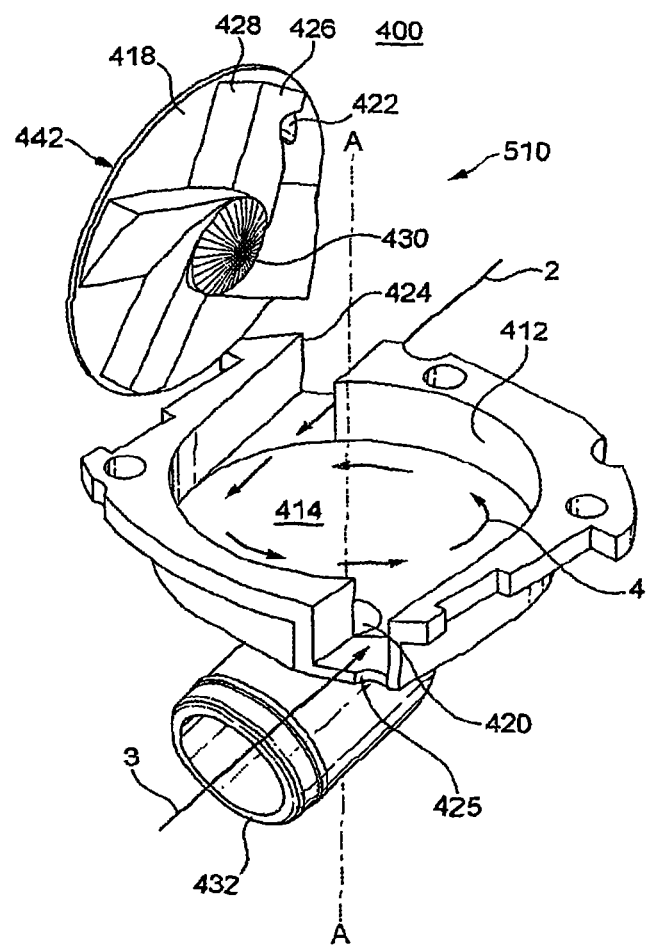
FIG. 4 shows a deagglomerator for use with airflow adaptor.

Referring to FIG. 4, the de-agglomerator (400) includes vanes (426) at the first end (418) of the swirl chamber (414) extending at least in part radially outwardly from the axis A of the swirl chamber. Each of the vanes (426) has an oblique surface (428) facing at least in part in a direction transverse to the axis A of the swirl chamber. The vanes (426) are sized such that at least a portion of the combined airflows 4 collide with the oblique surfaces (428). Preferably, the vanes comprise four vanes (426), each extending between a hub (430) aligned with the axis A and the wall (412) of the swirl chamber (414).

As shown in FIG. 4, the de-agglomerator (400) further includes an outlet port (432) for providing fluid communication between the second end (420) of the swirl chamber (414) and the airflow adaptor (not shown). A breath induced low pressure at the distal end of the airflow adaptor (not shown) causes the airflow through the supply port (422) and the airflows 2, 3 through the inlet ports and draws the combined airflow 4 through the swirl chamber (414). The combined airflow 4 then exits the swirl chamber (414) through the outlet port (432). Preferably the outlet port (432) extends substantially transverse to the axis A, such that the airflow 4 will collide with an inner wall of the outlet port (432) and create further turbulence.

During use of the de-agglomerator in combination with a breath-actuated dry powder inhaler including a dry powder delivery passageway and a dry powder reservoir for exposing a predetermined amount of dry powder to the delivery passageway, patient inhalation at the distal end of the airflow adaptor causes airflows 2 and 3 to enter through, respectively, the dry powder supply port (422) and the inlet ports. Although not shown, the airflow through the supply port (422) entrains the dry powder into the swirl chamber (414). The airflow and entrained dry powder are directed by the supply port (422) into the swirl chamber in a longitudinal direction, while the airflows 2 and 3 from the inlet ports are directed in a transverse direction, such that the airflows collide and substantially combine.

A portion of the combined airflow 4 and the entrained dry powder then collide with the oblique surfaces (428) of the vanes (426) causing particles and any agglomerates of the dry powder to impact against the oblique surfaces and collide with each other. The geometry of the swirl chamber (414) causes the combined airflow 4 and the entrained dry powder to follow a turbulent, spiral path, or vortex, through the swirl chamber. As will be appreciated, the decreasing cross-sections of the swirl chamber (414) continuously changes the direction and increases the velocity of the spiralling combined airflow 4 and entrained dry powder. Thus, particles and any agglomerates of the dry powder constantly impact against the wall (412) of the swirl chamber (414) and collide with each other, resulting in a mutual grinding or shattering action between the particles and agglomerates. In addition, particles and agglomerates deflected off the oblique surfaces (428) of the vanes (426) cause further impacts and collisions. The constant impacts and collisions cause any agglomerates to break into additional particles, and cause the particles to be substantially micronised.

Upon exiting the swirl chamber (414), the direction of the combined airflow 4 and the entrained dry powder is again changed to a transverse direction with respect to the axis A, through the outlet port (432). The combined airflow 4 and the entrained dry powder retain a swirl component of the flow, such that the airflow 4 and the entrained dry powder spirally swirls through the outlet port (432). Since the micronised powder and any remaining agglomerates maintain the swirl imparted from swirl chamber (414), the swirling flow causes additional impacts in the outlet port (432) so as to result in further breaking up of any remaining agglomerates prior to being inhaled by a patient.

Figure 5:
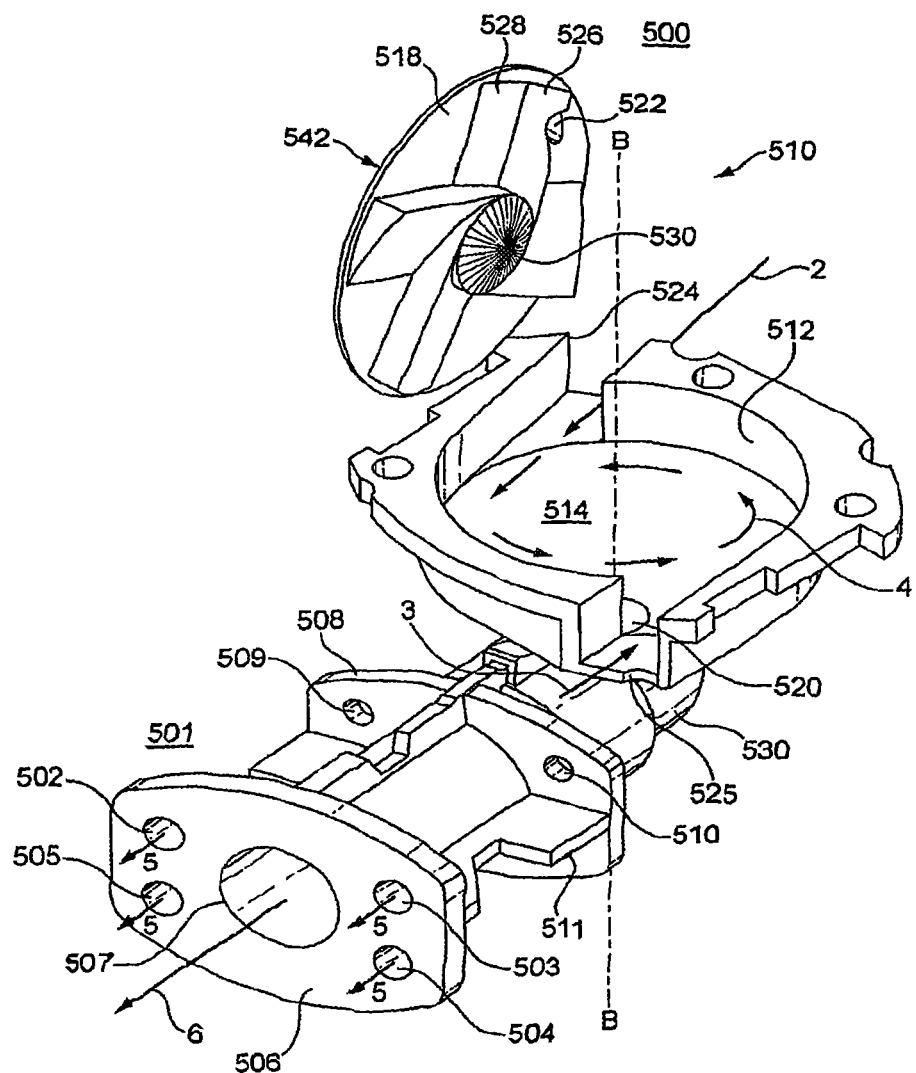
FIG. 5 shows a deagglomerator including a swirl chamber bypass port.

FIG. 5 shows a deagglomerator (500) including the airflow adaptor (501) according to the invention. The deagglomerator (500) comprises: an airflow adaptor (501) providing fluid communication between the outlet port (530) and a region exterior to the deagglomerator; an inner wall (512) defining a swirl chamber (514) extending along an axis (B) from a first end (518) to a second end (520); a dry powder supply port (522) in the first end (518) of the swirl chamber (514) for providing fluid communication between a dry powder delivery passageway of an inhaler and the first end (518) of the swirl chamber (514); at least one inlet port (524, 525) in the inner wall (512) of the swirl chamber (514) adjacent to the first end (518) of the swirl chamber (514) providing fluid communication between a region exterior to the de-agglomerator and the first end (518) of the swirl chamber; an outlet port (530) providing fluid communication between the second end (520) and the airflow adaptor (501); and at least one swirl chamber bypass port (502, 503, 504, 505). The at least one swirl chamber by-pass port (502, 503, 504, 505) allow air to flow (shown by arrows labelled 5) from a proximal end of the airflow adaptor to a distal end of the airflow adaptor (501) independently of the swirl-chamber (514) when a breath-induced low pressure is applied to the distal end of the airflow adaptor. The breath induced low pressure at the distal end of the airflow adaptor (501) also causes air to flow into the swirl chamber (514) through the dry powder supply port (522) and the at least one inlet port (524, 525). The combined airflow (arrow 4) leaves the airflow adaptor (501) through the conduit (507) (shown by arrow 6).

The at least one swirl chamber bypass port shown in FIG. 5 is in the form of four apertures (502, 503, 504, 505) in a first circumferential flange (506) of a conduit (507) of the airflow adaptor (501). The airflow adaptor (501) shown in FIG. 5 further comprises an optional second circumferential flange (508) which also comprises four apertures (509, 510, 511, fourth not shown). When present, in use, the apertures (509, 510, 511, fourth not shown) in the second circumferential flange (508) also form part of the swirl chamber bypass port.

Figure 3:
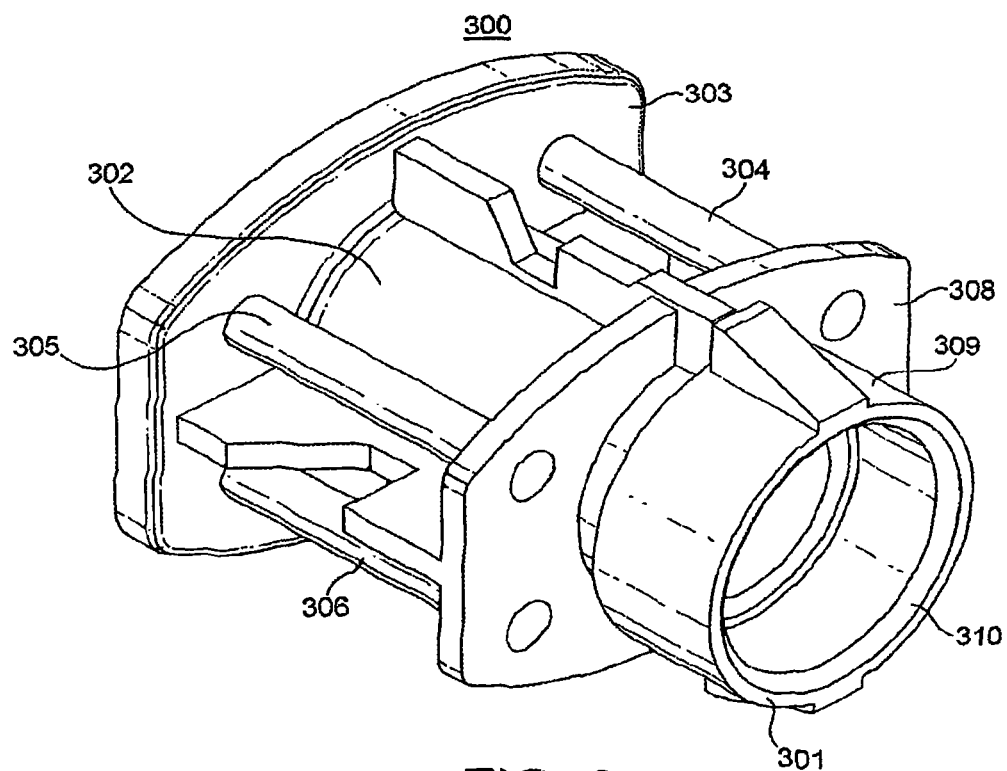
FIG. 3 shows an alternative embodiment of the airflow adaptor.

The airflow adaptor shown in FIG. 5 may be replaced by the airflow adaptor shown in FIG. 3. In such an arrangement the second conduits of FIG. 3 perform the function of swirl chamber bypass ports. Indeed any of the airflow adaptors described herein when combined with a deagglomerator as set out in FIG. 4 provide a swirl chamber bypass port.

Preferably, the ratio of the sum of the cross-sectional areas of the at least one swirl chamber bypass ports to the cross-sectional area of outlet port is such that that when a pressure breath induced low pressure is applied to the distal end of the airflow adaptor at least 5%, preferably at least about 15%, more preferably from about 5% to about 50%, more preferably from about 15% to about 40%, and even more preferably from about 20% to about 30% of the resulting airflow is directed through the at least one swirl chamber bypass port.

The percentage of airflow flowing through different parts of the airflow adaptor and deagglomerator may be calculated using methods known in the art. In particular they can be calculated by measuring the volumetric flow through an airflow adaptor according to the invention at a given pressure gradient and comparing it to the volumetric flow through a similar airflow adaptor with the same conduit, but with no means for allowing air to flow from a proximal end of the adaptor to a distal end of the adaptor independently of the airflow in the conduit when a breath induced low pressure is applied to the distal end of the airflow adaptor. In this instance, both measurements should be made with the same pressure gradient, preferably 4 KPa. The same method can be applied in the case of deagglomerators comprising airflow adaptors comprising swirl chamber by-pass ports. In this instance, however, it is the swirl chamber by-pass ports that are removed.

Suitable breath-actuated dry powder inhalers for including the deagglomerators and airflow adaptors of the present invention are disclosed in U.S. Pat. No. 6,748,947 and are sold under the trade name SPIROMAX™.

Figure 6:
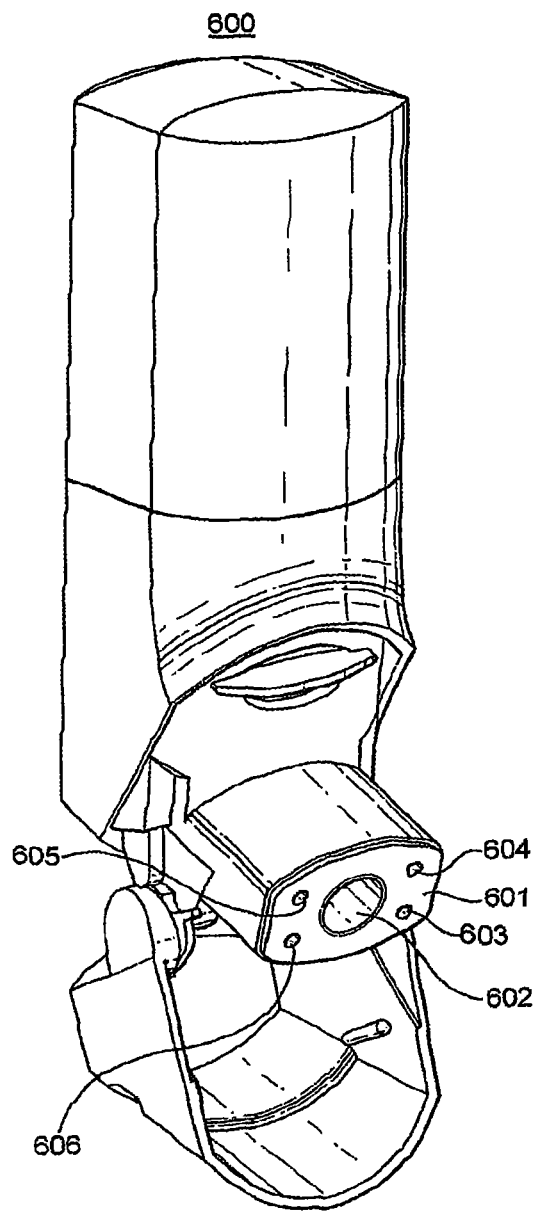
FIG. 6 shows a breath-actuated dry powder inhaler.

FIG. 6 shows the external appearance of a breath-actuated dry powder inhaler (600) according to the invention. The breath-actuated dry powder inhaler comprises an airflow adaptor (601) having a conduit (602) and four second conduits (603, 604, 605, 606). In this instance, the conduit (602) and the second conduits (603, 604, 605, 606) have circular cross-sections.

Figure 7:
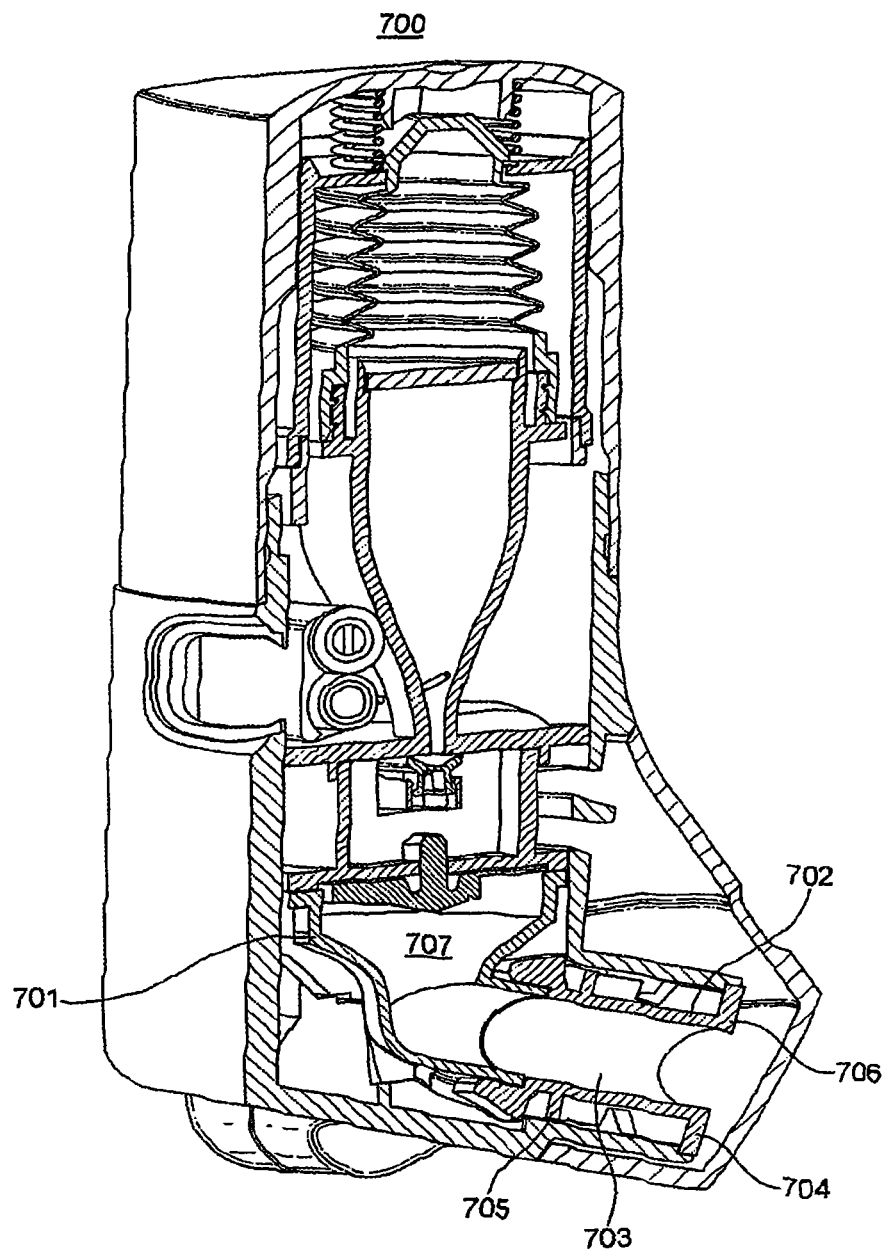
FIG. 7 shows a section through a breath-actuated dry powder inhaler.

FIG. 7 shows a breath-actuated dry powder inhaler (700) comprising a deagglomerator (701) including an airflow adaptor (702) according to the invention.

The airflow adaptor (702) comprises a conduit (703) with a first circumferential flange (704) comprising four apertures (not shown). The airflow adaptor further comprises a second circumferential flange (705) also comprising four apertures (not shown). The apertures in the first and second circumferential flanges perform the function of swirl chamber bypass ports. Accordingly, in use, a breath-actuated low pressure at the distal end (706) of the airflow adaptor (702) causes air to flow through the apertures (not shown) in the first (704) and second (705) circumferential flanges. The breath-actuated low pressure at the distal end (706) of the airflow adaptor (702) also causes air to entrain medicament and deliver it to the swirl chamber (707) via a supply port.

In use, a first breath-actuated airflow for entraining a dry powder from an inhaler is directed into a first end of a swirl chamber extending along a longitudinal axis from the first end to a second end. The first airflow is directed in a longitudinal direction. A second breath-actuated airflow is then directed in a substantially transverse direction into the first end of the swirl chamber such that the first and the second breath-actuated airflows collide and substantially combine. A portion of the combined airflows is then directed in a spiral path towards the second end of the swirl chamber, and all the combined airflows and any dry powder entrained therein are delivered through an outlet port in the second end of the swirl chamber to an airflow adaptor. A third breath-actuated airflow is directed to the airflow adaptor having by-passed the swirl chamber. Typically, in use, the third breath-actuated airflow will form before the first breath-actuated airflow is sufficient to entrain medicament.

Preferably, a portion of the combined first and second airflows is deflected off vanes non-rotationally fixedly attached to the first end of the swirl chamber and extending at least in part radially outwardly from the axis of the swirl chamber. Each of the vanes has an oblique surface facing at least in part in a direction transverse to the axis, such that the portion of the combined airflows is deflected in a substantially longitudinal direction towards the second end of the swirl chamber.

Typically, the dry powder medicament used in the breath-actuated dry powder inhaler comprises a medicament active selected from the group consisting of anti-inflammatory agents, anti-cholinergic agents, $\beta_2$-adrenoreceptor agonists, anti-infective agents, anti-histamines and combinations thereof.

Suitable anti-inflammatory agents include corticosteroids and NSAIDs. Suitable corticosteroids which may be used include those oral and inhaled corticosteroids and their prodrugs which have anti-inflammatory activity. Examples include methyl prednisolone, prednisolone, dexamethasone, fluticasone propionate, 6a, 9a-difluoro-17a-[(2-furanylcarbonyl) oxy]-11-hydroxy-16a-methyl-3-oxo-androsta-1,4-diene-17-carbothioic acid S-fluoromethyl ester, 6a, 9a-difluoro-11-hydroxy-16a-methyl-3-oxo-17a-propionyloxy-androsta-1,4-diene-17p-carbothioic acid S-(2-oxo-tetrahydro-furan-3S-yi) ester, beclomethasone esters (e. g. the 17-propionate ester or the 17,21-dipropionate ester), budesonide, flunisolide, mometasone esters (e. g. the furoate ester), triamcinolone acetonide, rofleponide, ciclesonide, butixocort propionate, RPR-106541, and ST-126. Preferred corticosteroids include fluticasone propionate, 6a, 9c-difluoro-11-hydroxy-16a-methyl-17a-[(4-methyl-1,3-thiazole-5-carbonyl) oxy]-3-oxo-androsta-1,4-diene-17,8-carbothioic acid S-fluoromethyl ester and 6a, 9a-difluoro-17a-[(2-furanylcarbonyl) oxyl-11-hydroxy-16a-methyl-3-oxo-androsta-1,4-diene-17p-carbothioic acid S-fluoromethyl ester, more preferably 6a, 9a-difluoro-17a-[(2-furanylcarbonyl) oxy]-11-hydroxy-16a-methyl-3-oxo-androsta-1,4-diene-17-carbothioic acid S-fluoromethyl ester.

Suitable NSAIDs include sodium cromoglycate, nedocromil sodium, phosphodiesterase (PDE) inhibitors (e. g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e. g. adenosine 2a agonists), cytokine antagonists (e. g. chemokine antagonists) or inhibitors of cytokine synthesis.

Suitable other (32-adrenoreceptor agonists include salmeterol (e. g. as the xinafoate), salbutamol (e. g. as the sulphate or the free base), formoterol (e. g. as the fumarate), fenoterof or terbutaline and salts thereof.

Suitable anticholinergic agents are those compounds that act as antagonists at the muscarinic receptor, in particular those compounds, which are antagonists of the M1 and M2 receptors. Compounds include the alkaloid of the belladonna plants as illustrated by the likes of atropine, scopolamine, homatropine, hyoscyamine; these compounds are normally administered as a salt, being tertiary amines.

Particularly suitable anticholinergics include ipratropium (e : g. as the bromide), sold under the name Atrovent, oxitropium (e. g. as the bromide), glycopyrrolate (e. g. as the bromide), and tiotropium (e. g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as H1-receptor antagonists) include any one or more of the numerous antagonists known which inhibit H1-receptors, and are safe for human use. All are reversible, competitive inhibitors of the interaction of histamine with H1-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows: Ethanolamines: carbinoxamine maleat, clemastine fumarate, diphenylhydramine hydrochloride, and dimenhydrinate.

Ethylenediamines: pyrilamine amleate, tripelennamine HCI, and tripelennamine citrate.

Alkylamines: chlropheniramine and its salts such as the maleate salt, and acrivastine.

Piperazines: hydroxyzine HCI, hydroxyzine pamoate, cyclizine HCI, cyclizine lactate, meclizine HCI, and cetirizine HCI.

Piperidines: Astemizole, levocabastine HCI, loratadine or its descarboethoxy analogue, and terfenadine and fexofenadine hydrochloride or another pharmaceutical acceptable salt.

Azelastine hydrochloride is yet another H1 receptor antagonist which may be used in combination with a PDE4 inhibitor.

Particularly suitable anti-histamines include methapyrilene and loratadine.

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (e.g. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving.

Additionally, medicament and/or excipient powders may be engineered with particular densities, size ranges, or characteristics. Particles may comprise active agents, surfactants, wall forming materials, or other components considered desirable by those of ordinary skill.

The invention claimed is:

1. An airflow adaptor for a breath-actuated dry powder inhaler, the airflow adaptor comprising:
    a first conduit having a proximal end and a distal end, wherein the proximal end allows fluid communication from a deagglomerator outlet port to the distal end of the first conduit,
    at least one second conduit for allowing air to flow from a proximal end of the adaptor to a distal end of the adaptor independently of the airflow in the first conduit when a breath induced low pressure is applied to the distal end of the airflow adaptor,
    a first circumferential flange at the distal end of the first conduit,
    at least one aperture in the first circumferential flange,
    a second circumferential flange at the proximal end of the airflow adaptor,
- at least one aperture in the second circumferential flange, and
- wherein the at least one second conduit comprises a tube connecting the at least one aperture in the first circumferential flange with the at least one aperture in the second circumferential flange.

2. An airflow adaptor according to claim 1 wherein a ratio of a sum of cross-sectional areas of the at least one second conduit to the cross-sectional area of the first conduit is such that when a breath induced low pressure is applied to the distal end of the airflow adaptor, at least 5% of the resulting airflow is through the at least one second conduit.

3. An airflow adaptor according to claim 1 wherein the first circumferential flange comprises two apertures.

4. An airflow adaptor according to claim 1 wherein a ratio of a sum of cross-sectional areas of the apertures in the second circumferential flange to the cross-sectional area of the first conduit is such that when a pressure breath induced low pressure is applied to the distal end of the airflow adaptor, at least 5% of the resulting airflow is through the apertures.

5. An airflow adaptor according to claim 1 wherein a ratio of a sum of cross-sectional areas of the at least one second conduit to the cross-sectional area of the first conduit is such that when a breath induced low pressure is applied to the distal end of the airflow adaptor, at least 20% of the resulting airflow is through the at least one second conduit.

6. An airflow adaptor according to claim 1 wherein the first circumferential flange comprises four apertures.

7. An airflow adaptor according to claim 1 wherein the second circumferential flange comprises four apertures.

8. An airflow adaptor according to claim 1 wherein a ratio of a sum of cross-sectional areas of the apertures in the second circumferential flange to the cross-sectional area of the first conduit is such that when a pressure breath induced low pressure is applied to the distal end of the airflow adaptor, at least 20% of the resulting airflow is through the apertures.

9. An airflow adaptor according to claim 1 further comprising two second conduits that are each in the form of a tube for allowing air to flow from a proximal end of the adaptor to a distal end of the adaptor independently of the airflow in the first conduit when a breath induced low pressure is applied to the distal end of the airflow adaptor.

10. A deagglomerator for a breath-actuated dry powder inhaler, the deagglomerator comprising an airflow adaptor according to claim 1.

11. A deagglomerator according to claim 10, the deagglomerator comprising:
- an inner wall defining a swirl chamber extending along an axis from a first end to a second end;
- a dry powder supply port in the first end of the swirl chamber for providing fluid communication between a dry powder delivery passageway of an inhaler and the first end of the swirl chamber;
- at least one inlet port in the inner wall of the swirl chamber adjacent to the first end of the swirl chamber providing fluid communication between a region exterior to the de-agglomerator and the first end of the swirl chamber;
- an outlet port providing fluid communication between the second end of the swirl chamber and the airflow adaptor;

wherein a breath induced low pressure at the distal end of the airflow adaptor causes air to flow into the swirl chamber through the dry powder supply port and the inlet port.

* * * * *